US00RE38081E

(19) United States
(12) Reissued Patent
Faithfull et al.

(10) Patent Number: US RE38,081 E
(45) Date of Reissued Patent: Apr. 15, 2003

(54) METHOD OF HEMODILUTION FACILITATED BY MONITORING OXYGENATION STATUS

(76) Inventors: Nicholas Simon Faithfull, 220 Coast Blvd., Suite 3A, La Jolla, CA (US) 92037; Peter E. Keipert, 13028 Harwich Ln., San Diego, CA (US) 92130; Duane J. Roth, 265 Coast Blvd., Suite 1, La Jolla, CA (US) 92037; Ronald M. Hopkins, 2223 Eucalyptus Ave., Escondido, CA (US) 92029

(21) Appl. No.: 09/776,144

(22) Filed: Feb. 2, 2001

Related U.S. Patent Documents

Reissue of:
(64) Patent No.: 5,865,784
Issued: Feb. 2, 1999
Appl. No.: 08/484,166
Filed: Jun. 7, 1995

(51) Int. Cl.[7] ..... A61M 37/00
(52) U.S. Cl. ..... 604/4.01; 604/6.14
(58) Field of Search ..... 604/4.01, 5.01, 604/6.01, 6.14, 6.11, 6.15, 16, 19, 27–8, 48, 59, 503, 506–508, 514, 518; 514/532, 6, 99, 109, 449, 743, 749, 759; 422/44–45

(56) References Cited

U.S. PATENT DOCUMENTS

| | | | |
|---|---|---|---|
| 3,482,575 | A | 12/1969 | Claff et al. |
| 3,958,014 | A | 5/1976 | Watanabe et al. |
| 3,975,512 | A | 8/1976 | Long |
| 4,073,879 | A | 2/1978 | Long, Jr. |
| 4,275,726 | A | 6/1981 | Schael |
| 4,301,144 | A | 11/1981 | Iwashita et al. |
| 4,473,494 | A | 9/1984 | Tye |
| 4,526,715 | A | 7/1985 | Kothe et al. |
| 4,600,531 | A | 7/1986 | Walder |
| 4,698,387 | A | 10/1987 | Schmidt et al. |
| 4,777,244 | A | 10/1988 | Bonhard et al. |
| 4,857,636 | A | 8/1989 | Hsia |
| 4,861,667 | A | 8/1989 | Estep |
| 4,911,999 | A | 3/1990 | Farmer et al. |
| 4,927,623 | A | 5/1990 | Long, Jr. |
| 4,963,130 | A | 10/1990 | Osterholm |
| 4,981,691 | A | 1/1991 | Osterholm et al. |
| 4,987,154 | A | 1/1991 | Long, Jr. |
| 5,080,885 | A | 1/1992 | Long, Jr. |
| 5,130,230 | A | 7/1992 | Segall et al. |
| 5,344,393 | A | 9/1994 | Roth et al. |
| 5,451,205 | A | 9/1995 | Roth et al. |
| 5,865,784 | A | 2/1999 | Faithfull et al. |

FOREIGN PATENT DOCUMENTS

| | | |
|---|---|---|
| EP | 091 183 A | 10/1983 |
| EP | 0 231 070 | 8/1987 |
| EP | 0 627 913 B1 | 4/1998 |
| FR | 2515198 | 4/1983 |
| JP | 58 32 829 | 5/1983 |
| JP | 60 166 626 | 1/1986 |
| WO | WO 81/00002 | 1/1981 |

OTHER PUBLICATIONS

Messmer et al. "Oxygen Supply to the Tissues During Limited Normovolemic Hemodilution" Res. Exp. Med. 159:152–166 (1973).

(List continued on next page.)

*Primary Examiner*—Jeffrey R. Jastrzab
*Assistant Examiner*—Patricia Bianco

(57) ABSTRACT

A method for hemodiluting a patient is disclosed which includes the steps of administering a biocompatible oxygen carrier in conjunction with surgery or organ ischemia or infarct while assessing the patient's $PvO_2$ or other oxygenation indices, and administering to the patient additional oxygen carrier or autologous blood in response to the $PvO_2$ value if necessary to maintain the $PvO_2$ at or above the desired level.

26 Claims, 5 Drawing Sheets

OTHER PUBLICATIONS

Colt, "The use of stroma–free hemoglobin solution for partial exchange transfusion in aortic resection in dogs", American J. of Surgery, 135:656–663 (1978).
Rice et al., "Blood and Blood Substitutes: Current Practice," *Advances in Surgery*, vol. 13, pp. 93–114, 1979.
Homer et al., "Oxygen Gradients Between Red Blood Cells in the Microcirculation," *Microvascular Research*, 22:308–323 (1981).
K. Fukushima et al., "Clinical Experience of Hemodilution with Fluosol–DA," *Jpn. J. Anesthesiol*, vol. 30, No. 7, pp. 741–745 (1981).
Riess et al., "Reassessment of Criteria for the Selection of Perfluorochemicals for Second–Generation Blood Substitutes: Analysis of Structure/Property Relationships," *Artificial Organs*, 8(1):44–56 (1984).
Winslow, R., "A Model for Red Cell $O_2$ Uptake," *International J. of Clinical Monitoring and Computing*, 2:81–93 (1985).
Federspiel et al., "A Theoretical Analysis of the Effect of the Particulate Nature of Blood on Oxygen Release in Capillaries," *Microvascular Research*, 32:164–189 (1986).
Gutierrez, "The Rate of Oxygen Release and its Effect on Capillary $O_2$ Tension: A Mathematical Analysis," *Respiration Physiology*, 63:79–96 (1986).
Messmer et al., "Present State of Intentional Hemodilution," *Eur. Surg. Res.*, 18:254–263 (1986).
Gould et al., "Fluosol–DA As a Red Cell Substitute in Acute Anemia," *New England Journal of Medicine*, 314(26): 1653–1656 (1986).
Biro et al., "The Effect of Hemodilution with Fluorocarbon or Dextran on Regional Myocardial Flow and Function During Acute Coronary Stenosis in the Pig," *Am. J. Cardiovascul. Pathol,*, 1:1:99–114 (1987).
Light et al., "Perfluorochemical Artificial Blood as a Volume Expander in Hypoxemic Respiratory Failure in Dogs," Chest, 9:3:444–449 (1987).
Riess et al., "Design, Synthesis and Evaluation of Fluorocarbons and Surfactants for in Vivo Applications: New Perfluoroalkylated Polyhydroxylated Surfactants" *Int'l Symposium on Blood Substitutes*, Montreal pp. 421–430 (1987).
Faithfull et al., "Peripheral Vascular Responses to Fluorocarbon Administration," *Microvascular Research*, 33:183–193 (1987).
Faithfull et al., "Critical Levels of $O_2$ Extraction Following Hemodilution with Dextran or Fluosol–DA," *J. of Critical Care*, 3:1:14–18 (1988).
Greenwalt et al., "Perioperative Red Blood Cells Transfusion," *JAMA*, 260:18:2700–2703 (1988).
Von Bormann, "Blutsparende Verahren—anästhesiologisch Aspekte," *Unfallchirurgie*, 4:194–200 (1989).
Zauder, "Preoperative Hemoglobin Requirements," *Anesthesiology Clinics of North America*, 8:3:471–480 (1990).
Zuck et al., "Autologous Transfusion Practice," *Vox Sang*, 58:234–253 (1990).
Vlahakes et al., "Hemodynamic Effects on Oxygen Transport Properties of a New Blood Substitute in a Model of Massive Blood Replacement," *J. Thorac. Cardiovasc. Surg.*, 100:379–388 (1990).
Sheffield et al., "Preparation and in Vivo Evaluation of Two Bovine Hemoglobin–Based Plasma Expanders," *Biotechnol. Appl. Biochem.*, 12:6:630–642 (1990).
Trouwborst et al., "Blood Gas Analysis of Mixed Venous Blood During Normoxic Acute Isovolemic Hemodilution in Pigs," *Anesth. Analg.*, 70:523–9 (1990).
Riess, "Fluorcarbon–Based in Vivo Oxygen Transport and Delivery Systems," *Vox Sang*, 61:225–239 (1991).
Stehling, "Acute Normovalemic Hemodilution," *Transfusion*, 31:9:857–868 (1991).
Mercuriali et al., "Autologous Blood," *Transmedica Europe Limited*, pp. 1–30 (1991).
Giordano et al., An Autologous Blood Program Coordinated by a Regional Blood Center: A 5–Year Experience, *Transfusion*, 31:6: 509–512 (1991).
Riess, "Overview of Progress in the Fluorocarbon Approach to In Vivo Oxygen Delivery," *Biomater. Artif. Cells Immobilization Biotechnol.*, 20:2–4:183–202 (1992).
Fennema et al., Myocardial Oxygen Supply Under Critical Conditions, The Effects of Hemodilution and Fluorocarbons, Adv. Exp. Med. Biol., 317:527–544 (1992).
Keipert et al., "Enhanced Oxygen Delivery by Perflubron Emulsion During Acute Hemodilution," *Artif. Cells Blood Substit. Immobil. Biotechnol.*, 22:4:1161–67 (1994).
Weiskoff, "Mathematical Analysis of Isovlemic Hemodilution Indicates That it Can Decrease the Need for Allogeneic Blood Transfusion," *Transfusion*, 35:1:37–41 (1995).
NIH Consensus Conference "Perioperative Red Blood Cell Transfusion" JAMA 260(18): 2700–2703 (1988).

METHOD OF HEMODILUTION FACILITATED BY MONITORING OXYGENATION STATUS

Matter enclosed in heavy brackets [ ] appears in the original patent but forms no part of this reissue specification; matter printed in italics indicates the additions made by reissue.

FIELD OF THE INVENTION

The present invention relates to improved medical procedures involving hemodilution. The improved method includes the administration of an oxygen carrier, the continuous monitoring of the mixed venous partial pressure of oxygen ($PvO_2$) or other tissue oxygenation indices, and the administration of autologous blood or additional oxygen carrier to maintain the $PvO_2$ or other indices at or above a predetermined level.

BACKGROUND OF THE INVENTION

More than 13 million units of blood are collected each year in the United States alone, and about 10 million of these units are transfused into 4 million recipients. Of the transfused units, about two-thirds are used during surgical procedures, and the remainder are used primarily for treating severe anemia or in emergency indications. Experience from clinical studies suggests that postoperative recovery can be shortened if hemoglobin concentrations are not allowed to fall to below 10 g/dL, the previously generally accepted indication for transfusion (Zauder, Anesth. Clin. North Amer. 8:471–80 (1990)). This criterion, however, is currently being reevaluated due in part to a recent increase in awareness of the risks associated with allogeneic blood transfusion (NIH Consensus Conference JAMA 260:2700–2703 (1988)). This has also resulted in a renewed interest in the use of autologous blood transfusion techniques, in particular predonation and cute normovolemic hemodilution (ANH).

Although autologous blood transfusion (i.e., reinfusion of the patient's own blood) was first employed over 170 years ago, it was not until the early 1970s that its use became more widespread because of growing concerns about the transmission of hepatitis. More recently, interest in autologous transfusions on the part of both patients and physicians has been stimulated by the emergence of AIDS. Despite an increased awareness and acceptance of the benefits of autologous blood transfusion, recent studies have revealed the widespread underutilization of autologous predonation (which is estimated to represent only 2–5% of all units drawn nationwide).

ANH is a procedure whereby several units of blood are withdrawn from the patient at the beginning of surgery and simultaneously replaced with either a crystalloid or a colloid plasma volume expander (Stehling et al. Transfusion 31:857 (1991)). The basic mechanism that compensates for most of the decreased oxygen capacity of the diluted blood is the rise in cardiac output and increased organ blood flow, factors that result from the improved fluidity of blood (i.e., lower viscosity) at lower hematocrit levels (Messmer et al Eur. Surg. Res. 18:254–263 (1986)). Weisskopf, Transfusion 35(1):37–41 (1995) describes a mathematical analysis of acute isovolemic hemodilution prior to surgical blood loss, which was used to determine the magnitude of potential reductions in allogeneic transfusion. Weisskopf concluded that isovolemic hemodilution prior to surgery can obviate allogeneic blood transfusion or diminish the amount transfused.

Predonation typically involves withdrawal of several units of a patient's blood during the six weeks prior to surgery. To avoid excessive anemia, the amount of blood that can be safely predonated in the weeks before surgery is limited, as is the amount of blood that can be removed during ANH.

Quite apart from ANH and predonation, it has been suggested that red cell substitutes, or blood substitutes, could be used in place of allogeneic blood (i.e., blood from other humans) during surgery. Methods for facilitating autologous blood use which employ a synthetic oxygen carrier or blood substitute are disclosed in U.S. Pat. No. 5,344,393 (Roth et al). Extensive research in the field of such blood substitutes over the past two decades has resulted in several candidate compositions. These include perfluorocarbon emulsions, such as FLUOSOL (Green Cross Corporation, Japan) and OXYGENT (Alliance Pharmaceutical Corp., San Diego, USA), and hemoglobin compositions, such as those derived from human, animal, or recombinant sources.

Traditional thinking has been that a red cell substitute would be given in volumes equal to the amount of whole blood that would be used for the same purpose. The use of such blood substitutes in large volumes to replace blood used in transfusions has not been entirely satisfactory in earlier applications. For example, early studies using FLUOSOL as a large volume blood substitute found that following blood loss, FLUOSOL was "unnecessary in moderate anemia and ineffective in sever anemia." Gould, et al., New Engl. J. Med. 314:1653 (1986). In this study, the average increase in arterial oxygen content with the drug was only 0.7 ml/deciliter. Thus, it was concluded that use of fluorocarbon emulsions as blood substitutes would not provide a significant benefit in severely anemic and bleeding patients. Indeed, although the U.S. Food & Drug Administration approved FLUOSOL in 1989 for use as a perfusion agent to enhance myocardial oxygenation during percutaneous transluminal coronary angioplasty (PTCA), it did not approve an earlier application for use as a large volume blood substitute for general use.

The problem in using fluorocarbon emulsions and hemoglobin compositions as red cell substituted or blood substitutes to compensate for blood loss from surgery, disease, or trauma lies in the relatively short circulating blood half life of those materials in vivo. Healthy humans typically require about two weeks to manufacture new red cells and increase their hematocrit to normal levels following blood loss. In contrast, the intravascular half life of fluorocarbon emulsions and hemoglobin substitutes in vivo is typically less than 72 hours, most often much less than 24 hours. Thus, even if sufficient quantities of a red cell substitute are administered during and/or after surgery, for example, to provide adequate oxygen delivery, the oxygen carrying capacity will drop significantly long before the body can compensate by making new red cells. One aspect of the current invention therefore defines an improved method to use red cell substitutes or blood substitutes for temporary short-time perioperative use in conjunction with autologous blood conservation strategies as a means of reducing or eliminating allogeneic blood transfusions.

Treatment of intracoronary thrombotic events such as myocardial infarcts usually involves systemic administration of thrombolytic agents, for example tissue plasminogen activator (tPA) or streptokinase. Mechanical intervention using percutaneous coronary angioplasty (PTCA) is also used. Under no circumstance during current treatment methods is blood purposefully diluted, as this would dilute the concentration of red blood cells and thus impair the delivery of oxygen to the hearts. Many cellular elements of blood, however, are detrimental in the case of myocardial infarction. For example, it is well known that platelets are necessary for the process of thrombus formation; reduction in the number of platelets would result in attenuation of the rate of thrombus formation following infarction. Further, certain white blood cells, polymorphonuclear leukocytes (neutrophils), are known to be activated at the site of the infarct to release cytotoxic components including oxygen free radicals, which, upon successful opening of the stenosed artery, are responsible for damaging normal cells through a phenomenon known as reperfusion injury. It would be beneficial, therefore, to dilute blood during and for a specified time after treatment of a myocardial infarction in order to reduce the number of platelets and neutrophils that exacerbate the effects of the infarct. Hemodilution is not done, however, because it is also necessary to maintain high red blood-cell levels to deliver oxygen to the myocardium.

The current invention therefore also defines an improved method to use red cell substitutes or blood substitutes for temporary short-term use in conjunction with treatment of myocardial infarction as a means of reducing or eliminating the detrimental effects associated with the infarct while providing enhanced oxygen delivery to the tissues.

SUMMARY OF THE INVENTION

The present invention provides a method for facilitating autologous blood use by a patient facing a loss of blood, comprising the steps of: removing and storing a portion of the patient's blood while intravenously administering a biocompatible liquid in sufficient quantity to bring the patient's blood hemoglobin level to a desired concentration; intravenously administering a biocompatible oxygen carrier, while periodically or continuously assessing the patient's tissue oxygenation, after which the patient undergoes a further loss of blood; and intravenously readministering the stored blood to the patient in response to the oxygenation measurements to maintain oxygenation measurements at or above a desired value. In one embodiment, the biocompatible liquid comprises a hemodiluent. In another embodiment, the hemodiluent is administered separately from the oxygen carrier. The method further comprises the step of administering additional oxygen carrier in response to the oxygenation assessments to maintain oxygenation assessments at or above a desired value prior to readministering the stored blood. The oxygen carrier is preferably derived from human, animal, plant, or recombinant hemoglobin, or it may be a fluorocarbon emulsion.

When the oxygen carrier is a fluorocarbon emulsion, the volume of the administered oxygen carrier is advantageously less than 50% of the volume of the biocompatible liquid. The fluorocarbon emulsion preferably has a concentration of at least 40%, preferably 50% or 60% w/v.

The biocompatible liquid is advantageously selected from the group consisting of a crystalloid, a colloid, a biocompatible oxygen carrier, and combinations thereof. The method also may further comprise the step of administering oxygen breathing gas to the patient during the procedure. The blood loss is often blood loss associated with surgery. Alternatively, the blood loss is associated with trauma.

The amount of oxygen carrier administered is usually between about 0.5 and 10 ml/kg, based on the body weight of the patient. The desired concentration of hemoglobin may advantageously be about 8 g/dL. The assessing of the patient's tissue oxygenation can be performed by assessing $PvO_2$, such as by using a pulmonary artery catheter. Preferably, the desired value of $PvO_2$ referred to above is about 40 mmHg.

The present invention also includes a method for the treatment of organ ischemia or infarct, including myocardial infarction, comprising the steps of removing a portion of the blood of a patient in need of treatment for organ ischemia or infarct and intravenously administering a biocompatible liquid in sufficient quantity to reduce the patient's blood hemoglobin level to a desired concentration; and intravenously administering a biocompatible non-red cell oxygen carrier in conjunction with the removing step to maintain oxygenation of the patient's tissues at or above a predetermined level. In one embodiment, the biocompatible liquid comprises a hemodiluent. In another embodiment, the hemodiluent is administered separately from the oxygen carrier. The oxygen carrier and biocompatible liquid may be the same or different, and may be as described above. The method advantageously also includes the step of administering oxygen breathing gas to the patient during the method. The amount of oxygen carrier administered is preferably between about 0.5 and 10 ml/kg, based on the body weight of the patient. As above, one preferred concentration of hemoglobin after hemodilution is about 8 g/dL. In order to assure adequate oxygenation of tissue including myocardium, the method further comprises the step of assessing the patient's tissue oxygenation by assessing $PvO_2$, as discussed above, to maintain a desired value of $PvO_2$ at a value, for example, of about 40 mmHg. In one modification of the method, the oxygen carrier constitutes at least a part of the biocompatible liquid.

In addition to the foregoing, the invention comprises a method of hemodiluting a patient, comprising the steps of removing and storing a portion of the patient's blood while intravenously administering a biocompatible oxygen carrier and periodically or continuously assessing the patient's tissue oxygenation, after which the patient undergoes a further loss of blood, and administering additional oxygen carrier to the patient in response to the oxygenation assessments to maintain the oxygenation assessments at or above a desired value. The method may further comprise the step of readministering the stored blood to the patient. The oxygen carrier and the desired values of oxygen carrier delivery and oxygenation may be as described above. The method may also include the step of administering oxygen breathing gas to the patient during the method.

Yet another aspect of the present invention comprises a method of hemodiluting a patient, comprising the steps of removing and storing a portion of the patient's blood while intravenously administering a biocompatible oxygen carrier and periodically or continuously assessing the patient's tissue oxygenation, after which the patient undergoes a further loss of blood. The method may further comprise the step of readministering the stored blood to said patient. The oxygen carrier and the desired values of oxygen carrier delivery and oxygenation may be as described above. The method may also include the step of administering oxygen breathing gas to the patient during the method.

DETAILED DESCRIPTION OF THE INVENTION

A. Overview of the Invention

Figure 1:
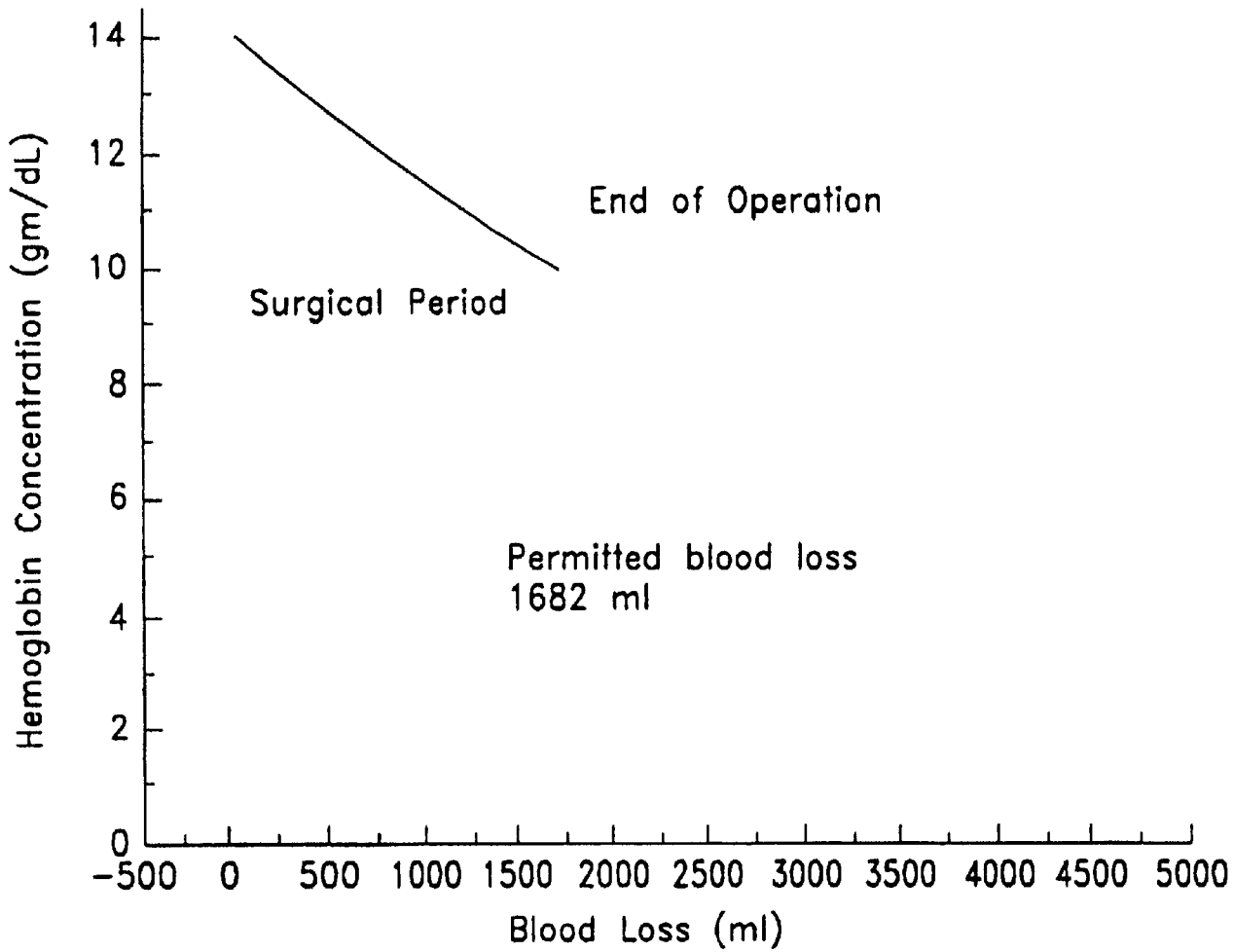
FIG. 1 is a graph showing acceptable blood loss during surgery without hemodilution, administration of allogeneic blood, or administration of a synthetic oxygen carrier, assuming a normal hemoglobin (Hb) concentration of 14 g/dL in the patient at the time of surgery, and a concentration of 10 dg/L being required at the end of operation. The calculated permitted blood loss before transfusion is deemed necessary amounts to 1682 l.

The invention described below combines the use of limited intravascular half-life oxygen carriers (blood substitutes) with hemodilution methods to increase allowable blood loss during surgery. Increasing the allowable blood loss decreases the need for autologous or allogeneic blood transfusion, thereby reducing or eliminating the attendant risks and complications. The invention also provides a method for adjunctive treatment of organ ischemia or infarct, including myocardial infarction, using hemodilution and administration of intravascular oxygen carriers.

In one method of the present invention, blood is removed from the patient prior to initiation of a surgical procedure, and the removed blood is stored for later readministration to the patient. The removed blood is replaced with an asanguineous fluid, generally crystalloid and/or colloid-based solutions which may also be the oxygen carrier red cell substitute based on hemoglobin (Hb) or fluorocarbon, to maintain normovolemia, while bringing the red cell contained hemoglobin concentration down to a predetermined level. At this point, the oxygen carrier is administered if not already administered as the hemodiluent during ANH. Additional blood is removed from the patient while monitoring the mixed venous partial pressure of oxygen ($PvO_2$) or other indices of global or regional tissue oxygenation. Tissue oxygenation can be assessed by use of oxygen electrodes, NADH fluorescence, or other means. When the $PvO_2$ or other index reaches a certain trigger level, surgery is initiated. During the surgical procedure $PvO_2$ or other oxygenation indices are continuously or periodically monitored and the autologous blood is added back to the patient in response to the oxygenation level to maintain that level at or above the trigger level. Alternatively, additional doses of the oxygen carrier can be administered until the maximum tolerated dose is reached.

The oxygen carrier is administered to the patient to supplement the oxygen-carrying capacity of the blood during or after hemodilution with crystalloid and/or colloid-based solutions, or the oxygen carrier can serve as the hemodiluent itself. In this clinical solution an additional margin of safety is afforded to the hemodiluted patient, by augmenting total oxygen delivery.

The combined use of autologous and blood substitute infusion technologies to avoid allogeneic transfusion is emphasized. The present invention contemplates use of both predeposit and perioperative autologous technologies with preferably less than one-to-one volume infusions of various oxygen-carrying blood substitute formulations. This invention includes use of any or all of these technologies in whatever order or of whatever magnitude they may be clinically useful in the preioperative clinical setting described.

Another aspect of the present invention provides a method useful in the treatment of organ ischemia or infarct, including myocardial infarction. Both blood oxygenation and dilution are accomplished for more beneficial adjunctive treatment. This aspect of the invention involves the hemodilution of the patient suffering organ ischemia with a generally crystalloid and/or colloid-based solutions. Blood is removed from the patient and replaced with an asanguineous fluid, while at the same time, the patient is administered an oxygen carrier red cell substitute, such as a fluorocarbon emulsion or hemoglobin solution. As before, the crystalloid or colloid-based solution may also be the oxygen carrier red cell substituted based on hemoglobin (Hb) or fluorocarbon. The administration of the oxygen carrier ensures adequate delivery of oxygen to the heart and other tissues, while hemodilution reduces the number of platelets, neutrophils and other cellular components that exacerbate the effects of the myocardial infarction. $PvO_2$ or other oxygenation indices are continuously or periodically monitored and additional doses of the oxygen carrier are administered until the maximum tolerated dose is reached in response to the oxygenation level to maintain that level at or above the trigger level.

The oxygen carrier is administered to the patient to supplement the oxygen-carrying capacity of the blood during hemodilution with crystalloid and/or colloid-based solutions. In this clinical situation total oxygen delivery is augmented while the number of detrimental cells in the blood is reduced.

One unique feature of the present invention is of particular importance. By monitoring the mixed venous partial oxygen pressure or other oxygenation indices during surgery or organ ischemia (rather than using conventional hemoglobin or hematocrit measurements), and by using a non-blood oxygen carrier, increased amounts of blood can safely be removed (below a conventional hematocrit-based transfusion trigger in the case of surgery). The present invention therefore increases the margin of safety of existing autologous transfusion technologies, by increasing the amounts of blood which can safely be lost during surgery, and more accurately determining the oxygenation status of the tissues. It also provides a method for augmenting oxygen delivery to the myocardium and other organs and tissues while reducing the number of cells in the blood which exacerbate the damaging effects of the ischemia or infarct.

B. Materials

A large number of materials suitable for use in the present invention are already known in the art. Without limiting the scope of the invention, certain representative materials are discussed below.

Several compositions have been proposed or demonstrated to function as intravenous oxygen carriers. These include fluorocarbon emulsions, including but not limited to perfluorocarbon emulsions. Such emulsions are typically fluorocarbon-in-water emulsions having a discontinuous fluorocarbon phase and a continuous aqueous phase. The emulsions typically include emulsifying agents and osmotic agents, together with buffers and electrolytes.

The fluorocarbon emulsion may be selected from a wide range of suitable emulsions. Preferably, it is a fluorocarbon-in-water emulsion, having a preferred fluorocarbon concentration of about 5% to about 125% weight per volume (w/v) that is used.

Fluorocarbons are fluorine substituted hydrocarbons that have been used in medical applications as imaging agents and as blood substitutes. U.S. Pat. No. 3,975,512 to Long discloses fluorocarbons, including brominated perfluorocarbons, used as a contrast enhancement medium in radiological imaging. Brominated fluorocarbons and other fluorocarbons are known to be safe, biocompatible substances when appropriately used in medical applications.

It is additionally known that oxygen, and gases in general, are highly soluble in some fluorocarbons. This characteristic has permitted investigators to develop emulsified fluorocarbons as blood substitutes. For a general discussion of the objectives of fluorocarbons as blood substitutes and a review of the efforts and problems in achieving these objectives see "Reassessment of Criteria for the Selection of Perfluorochemicals for Second-Generation Blood Substitutes: Analysis of Structure/Property Relationship" by Jean G. Reiss, Artificial Organs 8:34–56, (1984).

The fluorocarbon, in one preferred embodiment, is a perfluorocarbon or substituted perfluorocarbon. Fluorocarbon molecules used in these emulsions may have various structures, including straight or branched chain or cyclic structures, as described in Reiss, J., Artificial Organs 8(1): 44–56 (1984). These molecules may also have some degree of unsaturation, and may also contain bromine or hydrogen atoms, or they may be amine derivatives. The fluorocarbons may be present in the emulsion in any useful concentration, but usually range from about 5% to 125% W/V. As used throughout, concentrations defined as weight/volume are understood to represent grams/ml and % weight per volume to represent grams/100 ml.

Although concentrations as low as 5% w/v are contemplated, in a preferred embodiment the concentrations are at least 25% or 30%, preferably at least 40%, 50%, 55%, 60%, 75% or 80% w/v. Emulsions of 60%, 85%, 90%, and 100% are particularly preferred. Preferred fluorocarbon emulsion formulations are those disclosed in U.S. Pat. Nos. 4,865,836, 4,987,154, and 4,927,623, which are hereby incorporated by reference.

There are a number of fluorocarbons that are contemplated for use in the present invention. These fluorocarbons includes bis (F-alkyl) ethanes such as $C_4F_9CH{=}CH_4CF_9$ (sometimes designated "F-44E"), i-$C_3F_9CH{=}CH_6F_{13}$ ("F-i36E"), and $C_6F_{13}CH{=}CHC_6F_{13}$ ("F-66E") ;cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di- or F-trimethylbicyclo[3,3,1]nonane ("nonane"); perfluorinated amines, such as F-tripropylamine ("FTPA") and F-tri-butylamine ("FTBA"), F-4-methyloctahydroquinolizine ("FMOQ"), F-n-methyldecahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101").

Other suitable fluorocarbons may be selected from brominated perfluorocarbons, such as 1-bromo-heptadecafluoro-octane ($C_8F_{17}Br$, sometimes designated perfluorooctylbromide. "PFOB", or "perflubron"), 1-bromopenta-decafluoroheptane ($C_7F_{15}Br$), and 1-brmotridecafluorohexane($C_6F_{13}Br$, sometimes known as perfluorohexylbromide or "PFHB") Other brominated fluorocarbons are disclosed in U.S. Pat. No. 3,975,512 to Long, Also contemplated are fluorocarbons having nonfluorine substituents, such as perfluorooctyl chloride, perfluorooctyl hydride, and similar compounds having different numbers of carbon atoms, e.g., 6–12 carbon atoms.

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2$ $CFO(CF_2CF_2)_3OCF(CF_3)$, $(CF_3)CFO(CF_2CF_2)F$, $(CF_3)_2$ $CFO(CF_2CF_2)_2F$, $(C_6F_{13})_2$. Further, fluorocarbonhydrocarbon compounds, such as, for example compounds having the general formula $C_nF_{2n+1}C_{n'}F_{2n+1}$, $C_nF_{2n+1}OC_nF_{2n'+1}$, or $C_nF_{2n+1}CF{=}CHC_{n'}F_{2n+1}$, where n and n' are the same or different and are from about 1 to about 10 (so long as the compound or a mixture containing the compound is a liquid at room temperature). Such compounds, for example, include $C_8F_{17}C_2H_5$ and $C_6F_{13}$ $CH{=}CHC_6H_{13}$. It will be appreciated that esters, thioethers, and other variously modified mixed fluorocarbonhydrocarbon compounds are also encompassed within the broad definition of "fluorocarbon" materials suitable for use in the present invention. Mixtures of fluorocarbons are also contemplated. Additional "fluorocarbons" not listed here, but having those properties described in this disclosure that would lend themselves to use in vivo in accordance with the present invention are also contemplated.

Emulsifying agents used in the emulsions of this invention may be anionic, cationic or non-ionic surfactants or combinations thereof as are well known to those in the chemical arts, or they may be mixtures of synthetic compounds such as Pluronic F-68, a condensate of ethylene oxide with propylene glycol, as used in U.S. Pat. No. 4,073,879 to Long. Fluorosurfactants, such as those described by J. Riess et al. Int'l Symposium on Blood Substitutes, Montreal, (May 1987), are particularly suitable and can also be used. Emulsifying agents may also be mixtures of the above agents. Particularly suitable emulsifiers may include natural amphipathic compounds such as phospholipids, particularly phosphatidylcholine, wherein combined hydrophilic and hydrophobic properties enable the molecule to interface with both aqueous and fluorocarbon systems, thereby forming the emulsion droplets. There are various species of each class of phospholipids, such as the phospholipid cholines, comprising various pairings of saturated and unsaturated fatty acids in the glycerol structures. Phosphatidylcholine is an abutment natural material (lecithin) which may be purified from egg yolk, or may be produced synthetically (Avanti Polar Lipids, Pelham, Ala.). Phospholipid emulsifiers, particularly egg yolk phospholipid and lecithin, are particularly preferred.

The phospholipid emulsifying agent is typically included in the range of from 2 to 14% w/v, usually increasing the phospholipid concentration with increasing fluorocarbon concentration. The preferred amount for an emulsion comprising 75% w/v bromofluorocarbon is 2.5 to 5% w/v and 3.5 to 10% w/v of phospholipid for an emulsion with 100% w/v bromofluorocarbon. In a preferred embodiment, the phospholipid comprises at leas 2% w/v of the emulsion.

Emulsification requires large amounts of energy to convert a two-phase immiscible system into a suspension of discontinuous small droplets of hydrophobic fluid in an aqueous continuous phase. Fluorocarbon emulsification may be carried out generally by either of two general processes which provide energy to the system to break up the fluorocarbon volume into small droplets. In sonication emulsification, a probe is inserted into the mixture of fluorocarbon, emulsifier, and aqueous phase, and bursts of energy are released from the tip of the probe. In a mechanical emulsification process, such as that performed by a MICROFLUIDIZER apparatus (Microfluidics, Newton, Mass. 02164), streams of the mixed emulsion components are directed through the apparatus at high velocity and under high pressure (e.g. 15,000 psi), and the high shear forces or cavitation resulting from the mechanical stress applied to the fluid produce the emulsion.

The aqueous phase of the emulsion may have components dissolved therein which give the emulsion desirable properties. For example, it may comprise an osmotic agent to bring the emulsion to physiological isotonicity. The osmotic agent may be sodium chloride, or it may be a polyhydroxyl compound, such as a sugar or mannitol. The aqueous phase will also contain soluble buffering agents.

The liquid phase of the emulsion may also have components dissolved therein. For example, a phosphatidyl choline emulsifier may have glycerol, phosphatidyl glycerol, other phospholipids or cholesterol admixed, and further contain an antioxidant substance, such as a tocopherol, to protect against lipid oxidation.

Several fluorocarbon emulsions have been produced commercially for use as intravascular oxygen carriers. These include a mixed decalin emulsion formerly sold by Alpha Therapeutics Corp., Los Angeles, Calif. under the trademark FLUOSOL and perflubron-based emulsions produced by Alliance Pharmaceutical Corp. of San Diego, Calif., under the trademark OXYGENT.

One exemplary perflubron emulsion is a 90% (w/v) perflubron emulsion (Alliance Pharmaceutical Corp., San Diego, Calif.) having the following Formula I:

FORMULA I PERFLUBRON EMULSION

| Component | Percent (w/v) |
|---|---|
| Perflubron | 90.000 |
| Egg Yolk Phospholipid | 4.000 |
| $NaH_2PO_4.H_2O$, USP | 0.052 |
| $Na_2HPO_4.7H_2O$, USP | 0.355 |
| NaCl, USP | 0.280 |
| EDTA, USP | 0.020 |
| d-α-tocopherol, USP | 0.002 |
| Water for injection | 48.400 |

Hemoglobin compositions contemplated for use in the present invention are well known. Such compositions are disclosed, for example, in the following U.S. Patents, which are hereby incorporated by reference: U.S. Pat. Nos. 4,911,929; 4,861,867; 4,857,636; 4,777,244; 4,698,387; 4,600,531; 4,526,715; 4,473,494; and 4,301,144.

Various materials have been used successfully as plasma expanders in connection with hemodilution procedures. These include the well-known categories of crystalloid compositions (exemplified by Ringers-lactate and saline (0.9%) both from Baxter Healthcare Corp., Deerfield, Ill.) and colloid compositions. Colloid compositions include (1) modified fluid gelatins, such as those sold under the following trademarks: PLASMAGEL (R. Bellon Lab., Neuilly-sur Seine, France), GELIFUNDOL (Biotest, Frankfurt, Germany), GELOFUSINE (Braun, Melsungen, Germany) and HAEMACEL (Hoechst-Roussel Pharmaceutical Inc., Sommerville, N.J.); (2) dextran solutions, such as those sold under the trademarks MACRODEX (dextran-70) and RHEOMACRODEX (dextran-40) both from Pharmacia, Piscataway, N.J.; (3) albumin solutions, such as those sold under the trademark ALBUTEIN (Alpha Therapeutics, Los Angeles, Calif.) and human serum albumin (5%) from Abbott Labs. North Chicago, Ill.; (4) starch solutions such as Hetastarch (Hydroxyethylstarch), HAES (Fresenius, Hamburg, Germany) and HESPAN (DuPont, Willimington, Del.). These are administered in various volumes to maintain the patient's blood volume in the normal range and to encourage the increase in cardiac output that accompanies hemodilution procedures. In general, crystalloid-based solutions need to be given in volume ratios of 2:1 or 3:1 to blood withdrawn; colloids are usually given in lesser amounts.

C. Procedures

Autologous blood use virtually eliminates the possibility of contracting blood-borne diseases associated with transfusions as well as transfusion reactions occurring as a result of incompatibility between donor and recipient blood. Autologous blood for use in subsequent transfusions can be obtained in a number of ways, including one or more of the following: predeposit, perioperative isovolemic hemodilution; and intraoperative salvage.

Predeposit requires that the surgery be planned well in advance of the actual date. Blood is donated by the patient during the weeks before surgery, and is stored for subsequent administration to the patient. Phlebotomies of 350–400 ml are typically preferred at 2–7 day intervals, with the last collection more than 72 hours before surgery. The blood may be stored in the liquid state as whole blood, or it may be divided into red cells and plasma which can be frozen to preserve labile components.

Perioperative isovolemic hemodilution is the process of collecting blood immediately before a surgical procedure with the concomitant replacement by a sufficient volume of crystalloid or colloid solution. This practice decreases blood viscosity during surgery, thereby reducing the work load on the heart allowing cardiac output to rise and improving microcirculatory oxygen flow and distribution. Typically, sufficient blood is removed to reduce the hemoglobin concentration from a typical normal value of approximately 14 g/dL to about 10 g/dL. This blood is stored for readministration to the patient during or after surgery. After removal of some of the blood, or simultaneously with the removal, a crystalloid or colloid plasma expander (or both) is administered to the patient to maintain blood volume at a desired value, typically at the normal value.

Intraoperatively blood salvage involves collecting blood lost from a wound or body cavity during surgery, processing it, and reinfusing the processed blood into the same patient. This procedure is safe and effective if certain basic precautions are followed to ensure against contamination of the blood with bacteria or other pathogens, or malignant cells. Autotransfusion devices for collecting, filtering, and reinfusing the blood are commercially available. Also, some devices separate and wash the red blood cells, thereby avoiding administration of blood contaminated by debris, irrigating solutions, activated factors, anticoagulants, and free hemoglobin. Suitable devices of this type are exemplified by the Haemonetics Cell Separator and Cell Washer, Haemonetics Corp., Braintree, Mass.

Detailed reviews of autologous blood procedures and acute isovolemic or normovolemic hemodilution are found, for example, in Stehling, et al., Transfusion 31:857 (1991) and Mercuriali, et al, Autologous Blood, Transmedica Europe Limited, Eastbourne, United Kingdom (1991), which are hereby incorporated by reference.

In the practice of the present invention, autologous blood procedures (preferably involving perioperative hemodilution) are combined with administration of non-blood oxygen carriers, including hemoglobin compositions and, more preferably, fluorocarbon emulsions, together with the monitoring of the partial oxygen pressure in the venous blood ($PvO_2$) or other oxygenation indices in the patient.

Though it is generally acceptable that venous blood oxygen tension reflects, but does not measure, $PO_2$ of the tissue from which it is issuing, it is generally impractical, except under unusual circumstances, to monitor $PO_2$ in venous blood draining from individual tissues or organs. Hence, the mixed venous $PO_2$ ($PvO_2$) is usually taken as an acceptable estimator of the oxygen delivery/consumption ration in the whole body and is used as a guide to the oxygenation status of the whole body. It would be logical therefore to use $PvO_2$ as an indication for the need for blood transfusion during surgical procedures and in the trauma situation.

During the perioperative period, blood transfusions are routinely administered when a "critical" hemoglobin (Hb) concentration or hematocrit is reached. This level has traditionally been at a Hb concentration of 10 g/dL. To determine the lowest acceptable Hb level and the level of suitable transfusion trigger, it is necessary to first consider the changes that take place during hemodilution as blood is removed and normovolemia is maintained.

As a patient is hemodiluted, either intentionally as part of an autologous blood conservation program, or following surgical bleeding with maintenance of normovolemia, both Hb concentration and arterial $O_2$ content ($CaO_2$) decrease. As the red cell concentration falls, a reduction in whole blood viscosity occurs; this, together with the simultaneously occurring increase in venous return, causes a rise in cardiac output (CO) and in improvement in total $O_2$ transport to the tissues ($PO_2$). The degree to which this physiological compensation occurs will primarily depend on the response of CO to the reduction in red cell mass. Some authorities have concluded that the relationship between decrease in Hb concentration and CO is linear whereas others have maintained that it follows a curvilinear relationship; the degree of curvature found is very minimal, causing many researchers to perform calculations that assume a linear relationship.

In man, the extent to which cardiac output increases as Hb concentration decreases varies between 0.25 liters per minutes per gm of Hb change to 0.70 L/min/g. Hence, the cardiac output response to hemodilution differs between patients and this will affect the Hb level at which additional oxygen carrying capacity in the blood will be needed. The necessity for transfusion of red blood cells will also vary depending on such factors as vascular tone, which will cause the viscosity contribution to total systemic resistance to vary, and the ability of the myocardium to function at low Hb levels. During moderate hemodilution, myocardial blood flow increases proportionately more than total cardiac output and hence, in the absence of significant coronary atherosclerosis, no myocardial ischemia occurs. It has been shown, however, that low postoperative hematocrit (Hct) may be associated with postoperative myocardial ischemia in patients with generalized atherosclerosis. Though attempts have been made to define a critical Hct level, an empiric automatic transfusion trigger should be avoided and red cell transfusions should be tailored to the individual patient and be triggered by his or her own response to anemia.

As arterial blood passes through the tissues, a partial pressure gradient exists between the $PO_2$ of the blood in the arteriole entering the tissue and the tissue itself. Oxygen is, therefore, released from hemoglobin in the red blood cells and also from solution in the plasma; the $O_2$ then diffuses into the tissue. The $PO_2$ of the blood issuing from the venous end of the capillary cylinder will be a reflection of, but not necessarily equal to, the $PO_2$ at the distal (venous) end of the tissue through which the capillary passes. Under normal conditions this is essentially the same as that of interstitial fluid in contact with the outside of the capillary. The degree of equilibration between blood and tissue may depend on the speed of passage of blood through the capillary bed and under conditions of critical oxygen delivery caused by extreme anemia, there may not be time for equilibration of tissue and blood $PO_2$ levels; this may lead to higher than expected mixed venous $PO_2$ ($PvO_2$). Nevertheless, in the clinical situation, it is generally accepted that probably the most reliable single physiological indicator for assessing the overall balance between oxygen supply and demand is mixed venous oxygen tissues. It is therefore sensible to use $PvO_2$ as an indication of the overall adequacy of tissue oxygenation and to use it as a transfusion trigger rather than to use the traditional "10/30 rule" as an indication for red blood cell transfusion.

If $PvO_2$ is accepted as a reasonable indicator of patient safety, the question arises as to what can be considered a "safe" level of this parameter. Though much data exists on critical oxygen delivery levels in animals, there is little to indicate what a critical $PvO_2$ might be in the clinical situation. The available data indicates that the level is extremely variable. For instance, in patients about to undergo cardiopulmonary bypass, critical $PvO_2$ varied between about 30 mm Hg and 45 mm Hg; the latter value is well within the range of values found in normal, fit patients. Furthermore, shunting of blood in the tissues will cause elevated levels of $PvO_2$, such as is found in patients in septic shock, and will result in $O_2$ supply dependency.

A $PvO_2$ value of 35 mm Hg or more may be considered to indicate that overall tissue oxygen is adequate, but this is implicit on the assumption of an intact and functioning vasomotor system. This $PvO_2$ level is reached at a Hb of about 4 g/dL in patients with good cardiopulmonary function; even lower $PvO_2$ levels are tolerated in some patients when increased fractional inspired $O_2$ concentrations ($FiO_2S$) are employed. In each situation it is necessary to maintain a good margin of safety and it is best to pick a $PvO_2$ transfusion trigger at which the patient is obviously in good condition as far as oxygen dynamics are concerned.

Physiological and clinical studies involving measurement and calculation of oxygenation parameters are usually carried out using cardiac output measurements obtained by thermodilution using a pulmonary artery catheter such as a Swan-Ganz catheter. Oxygen delivery and oxygen consumption ($VO_2$) are then derived from measured or calculated arterial and mixed venous oxygen contents by using the Fick equation. The Fick equation allows the determination of oxygen consumption based on the difference between arterial and venous oxygen content times cardiac output. The equation is as follows:

$$VO_2=(C_aO_2-C_vO_2)\times CO$$

where VO=oxygen consumption, $C_aO_2$=arterial oxygen content, $C_vO_2$=venous oxygen content, and CO=cardiac output.

Accordingly, one embodiment of the present invention involves removal of a portion of the patient's blood, and administration of an intravenous fluid to reduce the patient's hemoglobin concentration from about the normal level of about 14 g/dL to a first "trigger" point. The intravenous fluid preferably includes a plasma expander, such as a colloid or crystalloid solution which may also be the oxygen-carrier red cell substitute or blood substitute based on Hb or PFC. This blood removal is usually deliberate, although the invention may also be used with trauma victims or other patients suffering involuntary blood loss. With deliberate removal, the blood is stored for readministration to the patient at a later time.

When the hemoglobin level reaches the first "trigger" point, an oxygen carrier is administered intravenously if not already done as part of the ANH procedure. Additional blood is then removed, and $PvO_2$ and/or other indicators of tissue oxygenation is continuously or periodically monitored, for example by using a pulmonary artery catheter, until the oxygenation reaches a second trigger point. At that time, autologous blood can be administered to the patient to maintain oxygenation at or above the second trigger point, or additional doses of the oxygen carrier can be given until the maximum tolerated dose is reached. In some instances, the patient will not reach the second trigger point as the initial dose of oxygen carrier is sufficient to maintain oxygenation above the second trigger point, and no additional oxygen carrier or autologous blood need be administered.

The oxygen carrier used is one other than red blood cells, preferably a biocompatible fluorocarbon emulsions of the type previously discussed, although hemoglobin compositions are also contemplated, as are other oxygen carriers.

Another aspect of the present invention provides for the use of a combination of hemodilution and administration of oxygen carrier as adjunctive treatment of organ ischemia or infarct, including myocardial infarction. Frequently, higher concentrations of inspired oxygen are given to a patient who has suffered a myocardial infarct to assure maximum saturation of hemoglobin in red blood cells and thereby maximum delivery of oxygen to damaged and potentially damageable myocardial tissue. Under no circumstance, however, is the blood purposefully diluted, as this would dilute the concentration of red blood cells and the ability of the blood to carry oxygen to the heart. This is so even though it is known that other cellular elements of the blood are detrimental, contributing to the damage caused by the myocardial infarct. Platelets, for example, are necessary for the process of thrombus formation. Neutrophils are known to be activated at the site of the infarct to release cytotoxic components, including free radicals, which are responsible for damaging normal cells.

Accordingly, it would be beneficial to dilute blood during and for a specified period of time after treatment of a myocardial infarct in order to reduce the number of platelets and neutrophils that exacerbate the effects of the myocardial infarct, provided that adequate oxygen delivery to the myocardium and other tissues can be maintained.

The method of the present invention provides for the hemodilution of a patient suffering from organ ischemia or infarct using a crystalloid- or colloid- based hemodiluent and intravenously administering a non-blood oxygen carrier such as a hemoglobin composition or a fluorocarbon emulsion. Alternatively, the hemodiluent may be the oxygen carrier. During hemodilution and the administration of the oxygen carrier, the patient's $PvO_2$ or other oxygenation indices is monitored, and the oxygen carrier is administered to maintain the $PvO_2$ or other oxygenation indices at or above a predetermined level.

This embodiment of the present invention involves removal of a portion of the patient's blood during and/or for a specified time during treatment of organ ischemia or infarct, and administration of an intravenous fluid to reduce the patient's hemoglobin concentrations from about the normal level of about 14 g/dL to a first "trigger" point. The intravenous fluid preferably includes a plasma expander, such as a colloid or crystalloid solution which may also be the oxygen-carrier red cell substitute or blood substitute based on Hb or PFC. The blood is stored for optional readministration to the patient at a later time. In one embodiment, where the intravenous fluid contains an oxygen carrier, no further hemodilution is done and the hemodilution procedure of the present invention is complete. The procedure reduces the quantity of circulating platelets and neutrophils, decreases the viscosity of the blood, and assures adequate perfusion of the tissue due to the added presence of the oxygen carrier.

In an optional embodiment of the organ ischemia or infarct treatment of the present invention, when the hemoglobin level reaches the first "trigger" point, an oxygen carrier is administered if not already done as part of the ANH procedure. Additional blood is then removed, and $PvO_2$ and/or other indicators of tissue oxygenation is continuously or periodically monitored, for example by using a pulmonary artery catheter, until the oxygenation reaches a second trigger point. At that time, additional doses of the oxygen carrier can be given until the maximum tolerated dose is reached to maintain oxygenation at or above the second trigger point, or the autologous blood can be administered to the patient.

In either hemodilution associated with surgery or hemodilution associated with the treatment of organ ischemia or infarct, the volume of intravenous fluid administered to the patient is at least about equal to 75%, preferably at least about 100% of the volume of blood removed from the patient. More preferably, the volume of intravenous fluid is between about 150% and 300% of the volume of blood removed, depending on whether the fluid is predominantly a colloid or a crystalloid and depending on whether it consists of or contains the oxygen carrier. Alternatively, the volume of intravenous fluid administered to the patient is adequate to reduce the hemoglobin concentration of the patient to the trigger levels discussed above.

In one embodiment of the invention, the intravenous fluid comprises a major portion of a plasma expander and a minor portion of oxygen carrier. The volume ratio of administered expander to an oxygen carrier will range from 0:1 to at least 10:1, depending on whether the fluid is a crystalloid or a colloid, and on the composition of the oxygen carrier, the concentration of the oxygen carrier, $PO_2$ and cardiac output. These ranges are most desirable when using a high concentration fluorocarbon emulsion, having at least about 40%, preferably at least about 50% or 60% fluorocarbon, w/v.

In one preferred embodiment, where a fluorocarbon emulsion such as perflubron-based emulsion is used as the oxygen carrier, the total amount of actual perfluorocarbon administration to the patient is advantageously from about 0.5 g/kg to about 10 g/kg, preferably 1–6 g/kg, based on the weight of the patient. When a 90% w/v or 100% w/v fluorocarbon emulsion is used, the volume of emulsion necessary to deliver the desired dosage is about 0.25 or 0.255 ml/kg to about 10 or 11 ml/kg, preferably about 1 to 6 ml/kg. Simple calculation provides the preferred volume of emulsion when different concentrations of fluorocarbon are used.

The hemodiluted patient is preferably administered a breathing gas enriched in oxygen, preferably at least 50–60%, and most preferably 75% or 100% oxygen. The effects of the enriched breathing gas, increased cardiac output due to hemodilution, the oxygen carrier, and the dissolved oxygen in the aqueous phase of the circulating intravascular fluid and plasma all combine to supply enhanced levels of oxygen to the patient. The collective contributions of these factors to oxygen delivery in the patient are discussed in more detail in section D, below.

During or after the surgical procedure or other condition resulting in blood loss, or following treatment of organ ischemia or infarct, the autologous blood removed from the patient (or the red cell portion thereof) can be readministered to the patient to maintain $PvO_2$ and/or other indices of oxygenation at or above the second trigger point. The oxygen carrier, meanwhile, is cleared from the circulation in a relatively short time, and its oxygen-carrying functions is supplanted by the autologous transfusion of red cells, if required.

Accordingly, there are various trigger points that are important to the use of the present invention. One is the hemoglobin or $PvO_2$ value at which oxygen carrier is infused if not already administered during the ANH. Others are the $PvO_2$ values at which additional doses of the oxygen carrier or transfusion with autologous blood are initiated. Appropriate values in any particular instance or for any particular type of procedure will be determined with consideration of such variables as age, sex, weight, cardiac status, disease state, and so forth. In general, however, one would expect that the first trigger point would occur during hemodilution at a hemoglobin level of between about 7 and 10 g/dL, typically at about 8 g/dL. (Alternatively, it could occur at a $PvO_2$ value of about 35 mm Hg to about 45 mm Hg, preferably at about 40 mm Hg). One would expect that the second trigger point would occur at a $PvO_2$ value of about 30 mm Hg to about 50 mm Hg, preferably at a value of about 40 mm Hg.

A comparison of the acceptable blood loss levels using conventional methods and the method of the present invention is shown in FIGS. 1–4.

FIG. 1 is a graph showing acceptable blood loss during surgery without hemodilution, administration of allogeneic blood, or administration of a synthetic oxygen carrier, assuming a normal hemoglobin concentration of 14 g/dL in the patient at the time of surgery, and a concentration of 10 g/dL being required at the end of surgery. The hemoglobin concentration is generally not allowed to fall postoperatively below about 10 g/dL. This allows a blood loss of 1682 mL before transfusion is deemed necessary.

Figure 2:
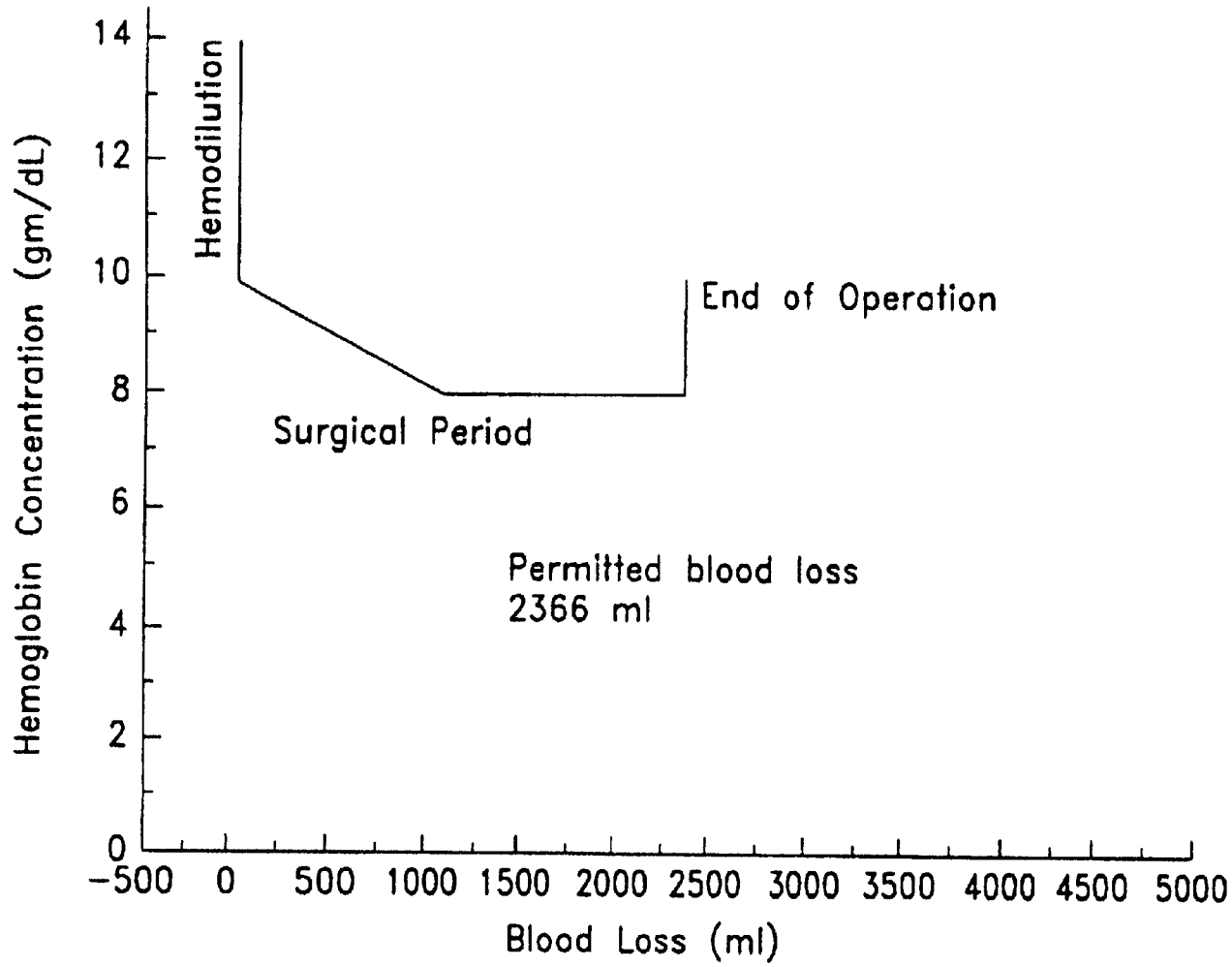
FIG. 2 is a graph showing acceptable blood loss during surgery using conventional hemodilution methods. It is assumed that no allogeneic blood is to be given, that initial ANH is to a Hb of 10 gm/dL. Intraoperative transfusion of ANH blood occurs at a Hb of 8 gm/dL and a Hb of 10 gm/dl is given at the end of operation. The calculated permitted blood loss amounts to 2366 ml.

FIG. 2 is a graph showing acceptable blood loss during surgery using conventional hemodilution methods, wherein the hemoglobin concentration is allowed to fall to a level of about 8 gm/dL. This method allows for blood loss up to about 2366 mL.

Figure 3:
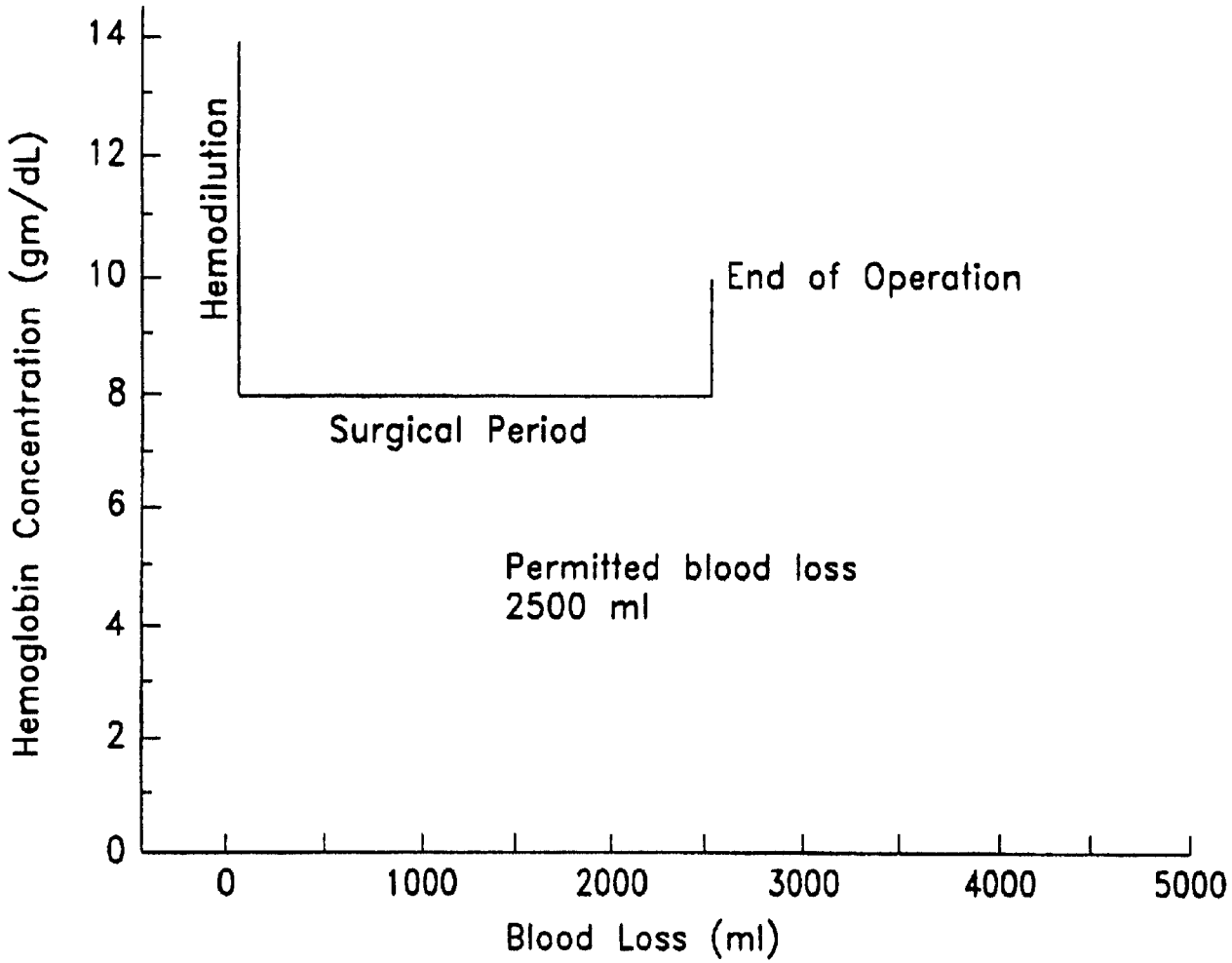
FIG. 3 is a graph showing acceptable blood loss during surgery using the method of isovolemic hemodilution described by Weisskopf, Transfusion 35(1) :37–41 (1995). This method allows a blood loss of 2500 ml.

FIG. 3 is a graph showing acceptable blood loss during surgery using the mathematical analysis described by Weisskopf. Transfusion 35(1):37–41 (1995). Assuming that hemodilution is completed before surgical blood loss is begun and that transfusion of removed blood is begun when surgical blood loss begins and lost blood is replaced at a rate that maintains the target hematocrit, this method allows for blood loss of 2500 mL.

Figure 4:
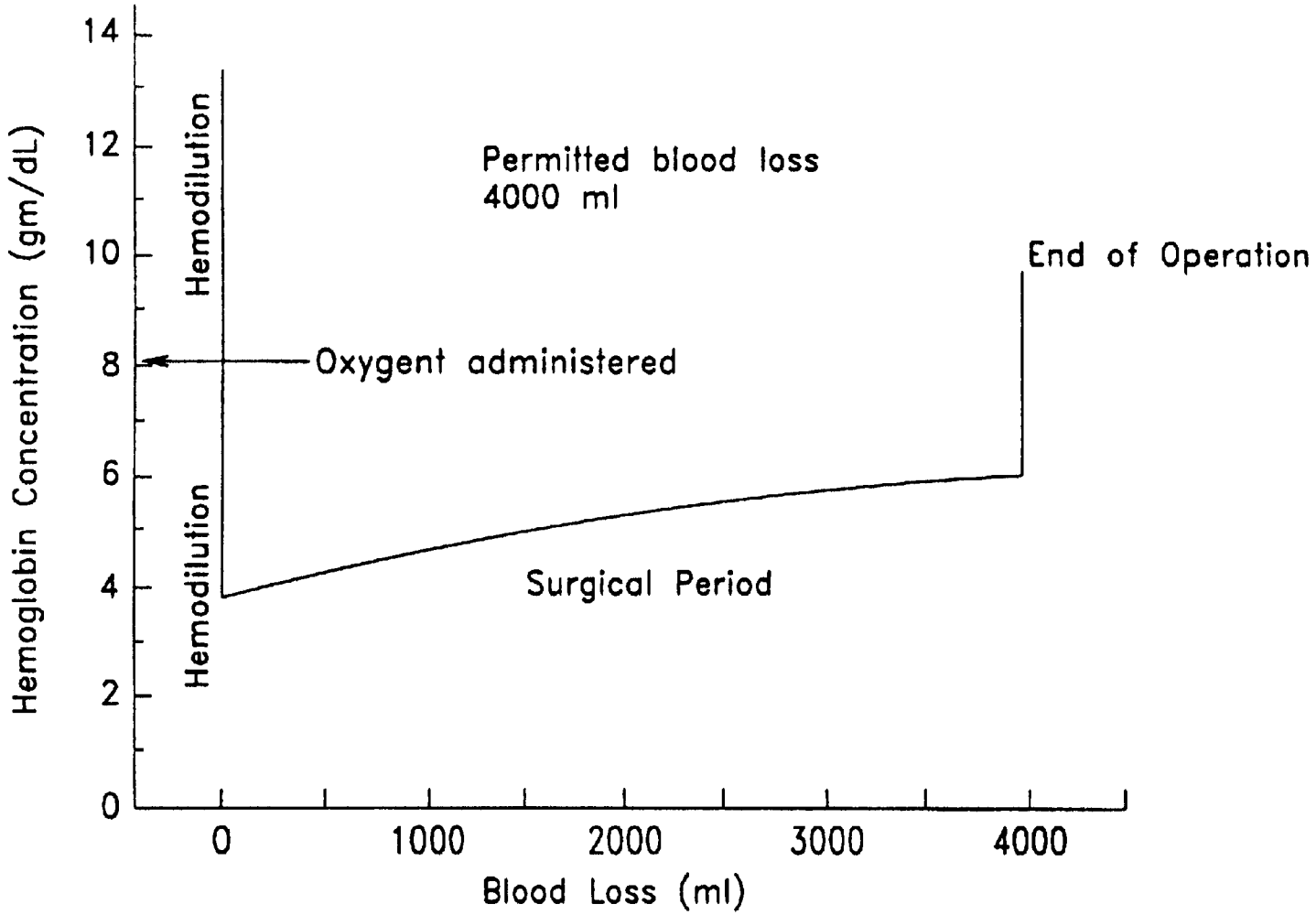
FIG. 4 is a graph showing acceptable blood loss during surgery using the method of the present invention, which allows a blood loss of 4000 ml. The present example uses 1.8 gm/Kg of a perflubron emulsion given at 8 gm/dL hemoglobin concentration. This method assumes that initial ANH is to a Hb concentration of 8 gm/dL. As surgical blood loss starts, ANH blood is transfused to keep the Hb at 8 gm/dL.

FIG. 4 is a graph showing acceptable blood loss during surgery using the method of the present invention. By monitoring $PvO_2$ levels or other indices of tissue oxygenation and using them as an indicator of the overall oxygenation status of the patient, rather than hemoglobin or hematocrit measurements, and by administering an oxygen carrier, blood loss can safely-be increased to 4000 mL. The present examples uses 1.8 gm/Kg of a perflubron emulsion given at 8 gm/dL hemoglobin concentration. This method assumes that initial ANH is to a Hb concentration of 8 gm/dL. As surgical blood loss starts, ANH blood is transfused to keep the Hb at 8 gm/dL.

D. Oxygen Delivery to Tissues

Although not intending to be bound by any particular theory of operation, the following discussion provides a framework for understanding the physical and physiological mechanisms contributing to the function of the present invention.

Oxygen transport to tissues can be considered to occur via two processes. The first is the convective (bulk) delivery of oxygen to tissues; the second is the delivery of oxygen to tissues via a diffusive process.

(1) Convective Oxygen Delivery

The first process, convective $O_2$ is described by the Fick equation:

$$VO_2=(C_aO_2-C_vO_2)\times CO$$

Although the Fick equation is quite straightforward, a number of physiological variables of importance are imbedded in it. For example, the arterial-venous differential in oxygen content $CAO_2$-$CvO_2$ is determined by the $O_2$ content of both arterial ($CaO_2$) and venous ($CvO_2$) blood, respectively, which, in turn, are directly related to the hemoglobin (Hb) concentration and the $O_2$ saturation and the contact of $O_2$ in the plasma. Oxygen saturation is determined by the $PO_2$ and by the position of the oxyHb (oxygenated form of Hb) dissociation curve. The $PO_2$ is determined by the $O_2$ tension in the inspired air and the capacity of the lung to oxygenate pulmonary capillary blood. Finally, the position of the oxyHb dissociation curve is determined by 2.3-diphosphoglycerate (2.3-DPG) as well as pH and $pCO_2$, which differ between arterial and venous blood and the temperature.

Similarly, cardiac output (CO) is controlled by many factors, including heart rate, the left ventricular filling volume and ejection fraction (i.e., stroke volume), and the demand for $O_2$ in tissues (i.e., oxygen consumption, $VO_2$). Assuming a constant blood volume and under stable hemodynamic conditions, the left ventricular filling volume is proportional to the blood viscosity, which, in normal humans, is primarily a function of the hematocrit (percent of red cells in blood).

Figure 5:
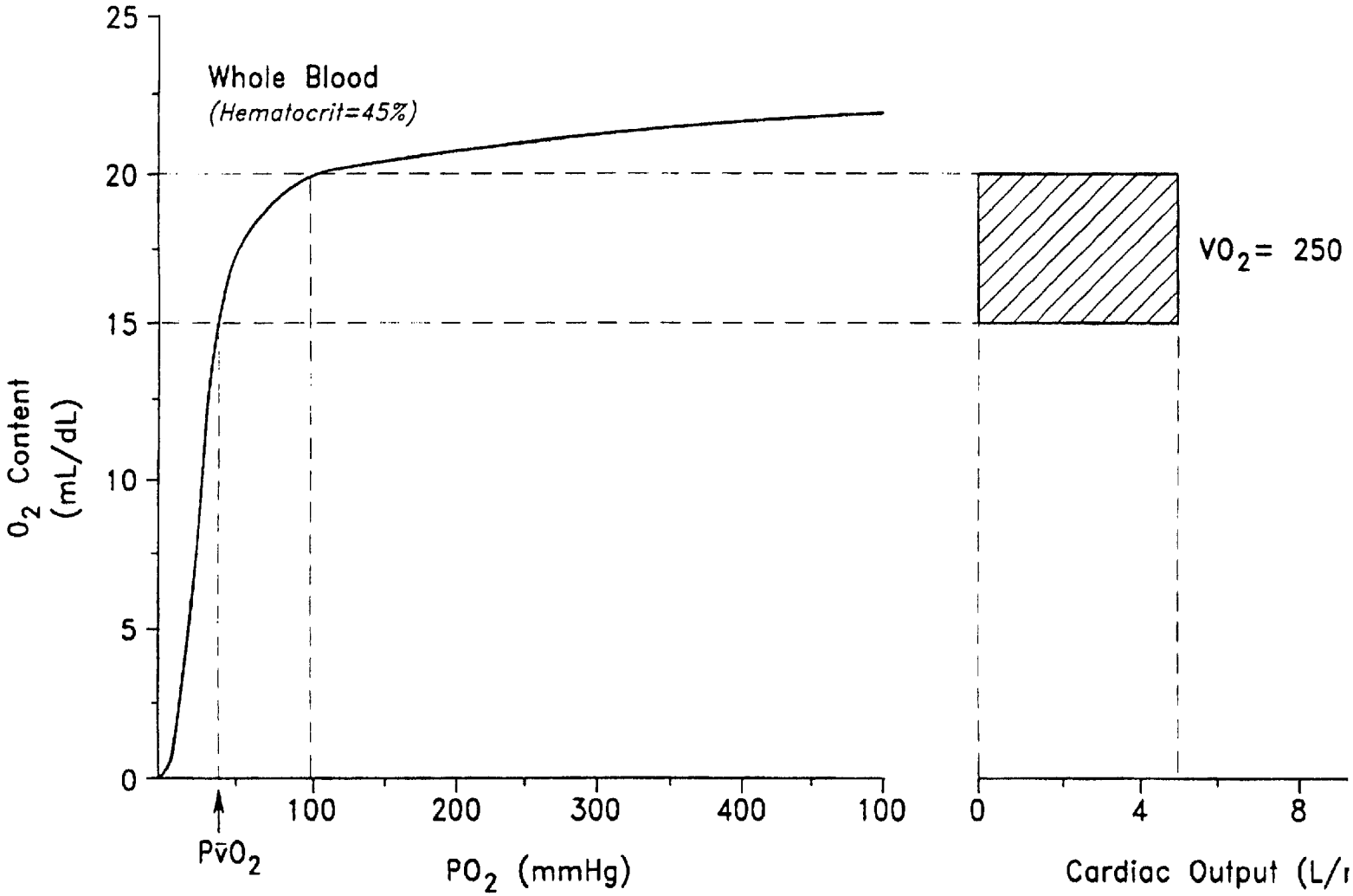
FIG. 5 is a graph showing the relationship between the $O_2$ delivery from the hemoglobin in blood and cardiac output under normal conditions (hematocrit=45%). Total $O_2$ utilization (or consumption; $VO_2$) is equal to the product of cardiac output times the arterial—venous $O_2$ content difference, and is indicated by the cross-hatched area. OxyHb dissociation curves were generated from data provided by the model developed by Winslow, Int. J. Clin. Monitor Comp. 2:81–93 (1985).

Some of these complex relationships can be shown graphically (see FIG. 5). In FIG. 5, $O_2$ content is placed against $O_2$ tension, $PO_2$ FIG. 5 presents data for a normal, 70 kg man at rest with a hemoglobin concentration of 14.4 g/dl (hematocrit=45%). The data for the oxyHb dissociation curve used to create this graphic representation were generated by the model developed by Winslow (1985), which calculates the total $O_2$ contents dissolved in the plasma and bound to hemoglobin. For a given arterial and venous $PO_2$ of 100 and 40 torr, respectively, the arterial to venous oxygen content difference ($CaO_2$–$CvO_2$) is 5 mL/dL. At a normal cardiac output of 5 L/min, the $O_2$ consumption ($VO_2$, represented by the cross-hatched area) is approximately 250 mL/min or 5 mL/kg/min.

Normally, more $O_2$ is delivered to tissue than is utilized, providing a "margin of safety". When the convective (bulk) delivery of $O_2$ decreases below a certain critical point, tissue function may be compromised, with various consequences such as tissue bypoxia, production of lactic acid, infarction, necrosis, etc. Once this critical oxygen delivery level is reached (i.e., when $O_2$ delivery is severely limited), then $VO_2$ (oxygen consumption) will be supply-limited. The actual value for the critical oxygen delivery level is very difficult to specify, since there are likely to be different values for different organs or different capillary beds.

When $O_2$ consumption is not supply-limited, changes in $O_2$ content of the arterial blood can be compensated for by other normal physiological mechanisms. For example, in anemia, the cardiac output becomes elevated (see below), as does the level of red cell 2.3-DPG. The latter serves to shift the oxyHb dissociation curve to the right (reduced affinity, increased $P_{50}$ [the $PO_2$ at which hemoglobin is 50% saturated with $O_2$])

A similar compensatory mechanism (with respect to the cardiac output) occurs during acute normovolemic hemodilution (Messmer et al. Res. Exp. Med. 159:152–56 (1986)). As the hematocrit decreases during the hemodilution, blood viscosity also decreases significantly, which allows the cardiac output to increase without any significant changes in the work load on the heart. In this way, total oxygen transport ($DO_2$) can be maintained.

Work by Guyton et al. (Cardiac Output and its Regulation, 2nd Ed. Saunders, Philadelphia (1973)) has shown that over a broad range, the cardiac output varies inversely with hematocrit. A hematocrit within the range of approximately 40 to 45% for normal, resting humans is considered most appropriate. When hematocrit values exceed 45%, blood viscosity limits cardiac output such that there is little beneficial effect from the additional $O_2$ carrying capacity of the increased number of circulating red cells. When the hematocrit is less than about 40%, the lower viscosity results in a decreased total peripheral resistance to blood flow which allows cardiac output to increase in order to maintain normal oxygen delivery.

It should be noted that augmenting $O_2$ transport by administration of a cell-free oxygen carrier differs from simple transfusion in several important ways. A key point in understanding the value of a low-dose acellular "blood substitute" is that plasma $O_2$ is increased, rather than red cell $O_2$, as is the case with transfusion of blood. Transfusion of red cells will increase bulk blood viscosity, which can cause a decrease in cardiac output and therefore may not increase the bulk $O_2$ delivery.

Addition of a cell-free $O_2$ carrier, on the other hand, will increase bulk $O_2$ delivery by elevating the $O_2$ content of the plasma and potentially increasing the cardiac output (since overall blood viscosity would be reduced). This additional contribution to $DO_2$ is primarily due to an increased amount of $O_2$ dissolved in the plasma compartment. $DO_2$ can be further increased by addition of a dose of perflubron emulsion or other oxygen carrier under these conditions which would provide an even greater margin of safety.

As a result, the hematocrit and hemoglobin levels can be significantly decreased when compared with the prior art methods, since the hemoglobin and hematocrit measurements do not adequately reflect oxygen carried in the added liquid volume and carried by the oxygen carrier. Nor do they account for increased cardiac output which follows from hemodilution. $PvO_2$ measurement, therefore, is a better indicator of the oxygenation status of the patient.

(2) Diffusion Oxygen Delivery

Oxygen transport to tissue also occurs via diffusion. There are a series of diffusion boundaries through which $O_2$ must pass on its way from the red cell to the tissues. Fick's law of diffusion states that the overall rate of diffusion of a gas from one compartment to another is governed by the diffusion gradient, the difference between the gas concentrations ($P_1$–$P_2$) within the two compartments, and a diffusion constant, $K_d$, which is a lumped-sum reflection of many factors including properties of the boundary layers, temperature, etc.

$$\frac{d(O_2)}{dt} = K_d(P_c - P_t)$$

The process of $O_2$ diffusion can be simply illustrated by considering the movement of water through holes in a wall separating a higher elevation reservoir and a lower level reservoir. Water is supplied initially at one elevation ($P_1$), and flows to a second lower level ($P_2$). The hydrostatic pressure driving this movement is the vertical difference in height between the two reservoirs. The total rate of water movements is also limited by the cross-sectional area of the holes in the barrier which provide resistance to flow from compartment 1 to 2. In this analogy, the two water levels correspond to the two $O_2$ pressures ($P_1$ and $P_2$) in Fick's law of diffusion, shown above, and the cross-sectional area of the holes in the barrier (through which the water flows) would be represented by the diffusion constant, $K_d$.

Experimental work has shown that there are probably two barriers to diffusion of $O_2$ from the red cell to the tissues; the layer of unstirred plasma surrounding the red blood cell, and the collective membranes separating the plasma space from the cellular cytosol of adjacent tissue. Raising the $PO_2$ in the plasma will have the effect of increasing the rate of diffusion into tissues, since the plasma represents an "intermediate level reservoir" in the preceding analogy. In fact, if there is not a limiting supply of $O_2$ in red cells, then the rate of movement of $O_2$ from plasma to tissues will be proportional to this plasma reservoir. This represents the essence of the proposed use of low-dose $O_2$ carriers to reduce the need to transfuse allogeneic blood.

The proposed mechanism assumes that a small reduction of the reservoir of available $O_2$ (e.g., hemodilution) will not appreciably change the overall rate of diffusion because it is assumed that the barrier to diffusion represented by the membranes between the plasma and tissue cytosol space is rate-limiting. Experimental evidence exists to support this assumption.

Increasing the diffusive delivery of $O_2$ to tissue is sometimes called "diffusion facilitation", and could increase $O_2$ delivery to tissues under conditions where $O_2$ delivery might be otherwise supply-limited. In other words, increasing the dissolved (plasma) $O_2$ concentration is expected to decrease the level at which critical $O_2$ delivery occurs and thereby increase the margin of safety in terms of prevention of tissue hypoxia. Experimental evidence suggests that this is, in fact, the case. In a study by Faithfull & Cain (J. Crit. Care 3:14–18 (1988)), dogs were initially hemodiluted with either 6% dextran (average molecular weight 70,000, in Tyrode's solution), or the perfluorocarbon emulsion, FLUOSOL, and then progressively hemorrhaged to determine the critical $O_2$ extraction ratios. FLUOSOL-treated dogs had lower mixed venous $PO_2$ levels and higher $O_2$ extraction fractions at the critical $O_2$ delivery point. This indicated that perfluorochemicals in FLUOSOL may have promoted diffusion of $O_2$ into the tissues. This effect was very evident in these FLUOSOL studies since these dogs likely had a compromised microcirculation due to the severe capillary flow inhomogeneity that occurs in dogs immediately following injection of only 1 to 2 mL of the FLUOSOL emulsion (Faithfull et al. Microvasc. Res. 33:183–93 (1987)).

It should be noted that transfusion of red cells will not affect $O_2$ diffusion in the same manner as described. In fact, an additional physiological effect described by Federspiel et al. (Microvasc. Res. 32:164–89 (1986)), refers to the fact that in normal capillary beds, red cells are separated by considerable distances as they individually traverse the capillary network. The $O_2$ would be expected to transfer from red cells to tissue predominantly across the area where the red cell is closely in contact wit the endothelial cells lining the vasculature. Addition of a cell-free $O_2$ carrier might increase the rate of $O_2$ transfer, simply on the basis that more $O_2$ would be in contact with the endothelial cells.

In general, improvement of blood fluidity by hemodilution has been shown to increase mean tissue $PO_2$ in various organs (Messmer et al. Res. Exp. Med. 159:152–56 (1973)). This increase in tissue $PO_2$ was attributed to more even flow distribution at the microcirculatory level and was interpreted as improved tissue oxygenation. On the other hand, Homer Microvasc. Res. 22:308–23 (1981), argued that in acute anemia there may be large differences between red blood cell $PO_2$ and the plasma $PO_2$. This would occur as a result of $O_2$ diffusion from the red cell being slowed by passage through the plasma (which has very low $O_2$ solubility characteristics). With hemodilution, the spacing between red blood cells in tissue capillaries is increased so that outward diffusion of $O_2$ from red cells is slowed further by the increased diffusional barrier of plasma. The resultant gradient for $PO_2$ may not be resolved (i.e., not all the oxygen has time to unload) during the short time that the red cell dwells in the capillary and $O_2$ extraction may be diminished accordingly (Gutierrez, Respirat. Physiol. 63:79–96 (1985)).

The presence of an additional $O_2$ carrier such as a perfluorochemical in the plasma will increase the total $O_2$ content in the plasma compartment of blood and may facilitate the diffusion of $O_2$ from the red cell into the tissues. The addition of a relatively small dose (3 mL [2.7 g perflubron]/kg BW) of a concentrated 90% w/v perflubron emulsion will result in a significant increase in the total $O_2$ content in the plasma. When performed during respiration with 100% $O_2$ and in the presence of acute normovolemic hemodilution (to a hematocrit of 25%), the net result would represent an increase in the available oxygen. Normal oxygen consumption would come preferentially from the perflubron and the plasma, since this $O_2$ is physically dissolved and therefore readily available (compared to the $O_2$ that is chemically bound to hemoglobin as a ligand). The remaining $O_2$ carried by the red cells would therefore represent an available reservoir of extra $O_2$ that would supply additional oxygen, when needed, to prevent certain sensitive tissues from reaching a critical level of $O_2$ delivery.

A low-dose cell-free oxygen carrier is therefore superior, in terms of tissue oxygenation, to additional red cell transfusion. Such an oxygen carrier is used for the temporary enhancement of oxygen delivery during the acute phase of surgery or following organ ischemia or infarct. None of the currently available oxygen carriers can be considered effective "blood substitutes" because of their short retention time in the circulation (hours) compared to red cells (months). With routine use, especially in uncomplicated elective surgery combined with acute normovolemic hemodilution procedures, the "transfusion trigger" can be reduced. With the method of the present invention, wherein $PvO_2$ or other indices of tissue oxygenation is continuously or periodically monitored and autologous blood or additional oxygen carrier administered to the patient in response to $PvO_2$ levels, the "transfusion trigger" can be reduced even further. This can eliminate the need for translation of allogeneic red blood cells in many cases and thereby significantly reduce the risk of transfusion-borne disease and transfusion reaction. The present invention also provides for hemodilution as an adjunctive therapy for organ ischemia or infarct, by maintaining adequate delivery of oxygen to the tissues while reducing the number of cells known to excaberage the effects of ischemia and infarct.

EXAMPLE 1

Enhancement of $O_2$ Delivery by Perfluorocarbon Emulsion

Immediately prior to undergoing surgery, a patient is subjected to perioperative isovolemic hemodilution. The removed blood is stored for later use. Blood is removed with the concomitant intravenous replacement by a crystalloid solution. During this time, the patient's fractional inspired oxygen concentration ($FiO_2$) is increased to 1. The patient is hemodiluted until the hemoglobin concentration reaches 8 gm/dL, with each aliquot of the removed blood being replaced by 3 volumes of Ringer-lactate. A 90% w/v perflubron emulsion having the composition of Formula I is administered intravenously to a total dose of 1.8 gm/kg body weight, while the patient's $PvO_2$ is monitored using a Swan-Ganz catheter. Hemodilution and administration of perflubron emulsion is continued until the $PvO_2$ reaches 40 mm Hg (hemoglobin level is 2 gm/dL). Surgery is then initiated, with an attendant blood loss of up to 3 liters. Autologous blood is then re-administered to the patient to maintain the $PvO_2$ at 40 mm Hg or above.

Although the invention has been described with reference to particular preferred embodiments, the scope of the invention is defined by the following claims and should be construed to include reasonable equivalents.

What is claimed is:

1. A method of hemodiluting a patient, comprising the steps of:

removing and storing a portion of the patient's blood [while intravenously] *and* administering a biocompatible oxygen carrier, after which the patient undergoes a further loss of blood wherein the removal and further loss of blood reduces the patient's [hematocrit value] *hemoglobin concentration* to about 8 g/dL or below;

monitoring the patient's tissue oxygenation status during said removal and further loss of blood, whereby the patient's [hematocrit value] *hemoglobin concentration* is maintained at a level of about 8 g/dL or below; and administering additional biocompatible oxygen carrier to the patient during or after said further loss of blood in response to said oxygenation status to maintain said oxygenation status at or above a desired value.

2. The method of claim 1, further comprising the step of readministering blood removed during said removing step to said patient.

3. The method of claim 1, wherein the oxygen carrier is derived from human, animal, plant, or recombinant hemoglobin.

4. The method of claim 1, wherein the oxygen carrier is a fluorocarbon emulsion.

5. The method of claim 4, wherein said fluorocarbon emulsion has a concentration of at least 40%, w/v.

6. The method of claim 4, wherein the concentration of said fluorocarbon emulsion is at least 60%, w/v.

7. The method of claim 1, further comprising the step of administering oxygen breathing gas to the patient during said method.

8. The method of claim 1, wherein the amount of oxygen carrier administered is between about 0.5 and 10 ml/kg, based on the body weight of the patient.

9. The method of claim 1, wherein said monitoring step is performed by assessing $PvO_2$.

10. The method of claim 9, wherein said assessing of said patient's $PvO_2$ is performed using a pulmonary artery catheter.

11. The method of claim 9, wherein said desired value of $PvO_2$ is about 40 mmHg.

12. The method of claim 1, wherein said monitoring step is performed periodically.

13. The method of claim 1, wherein said monitoring step is performed continuously.

14. A method of hemodiluting a patient, comprising the steps of:

removing and storing a portion of the patient's blood [while intravenously] *and* administering a biocompatible oxygen carrier;

simultaneously monitoring the patient's tissue oxygenation status, wherein biocompatible oxygen carrier is administered so that said tissue oxygenation status is maintained at or above a desired value;

stopping removal of the patient's blood when the hemoglobin concentration in the patient reaches a point corresponding to [a hematocrit value of] about 8 g/dL or below;

continuing to monitor the patient's tissue oxygenation status while allowing the patient to undergo a further loss of blood, whereby the patient's [hematocrit value] *hemoglobin concentration* is maintained at a level of about 8 g/dL or below; and

[intravenously] readministering blood removed during said removing step in an amount sufficient to maintain said oxygenation level at or above a desired value and concomitantly increasing said [hematocrit value] *hemoglobin concentration* above 8 dg/L.

15. The method of claim 14, further comprising the step of administering additional biocompatible oxygen carrier to said patient following said further loss of blood.

16. The method of claim 14, wherein the oxygen carrier is derived from human, animal, plant, or recombinant hemoglobin.

17. The method of claim 14, wherein the oxygen carrier is a fluorocarbon emulsion.

18. The method of claim 17, wherein said fluorocarbon emulsion has a concentration of at least 40%, w/v.

19. The method of claim 17, wherein the concentration of said fluorocarbon emulsion is at least 60%, w/v.

20. The method of claim 14, further comprising the step of administering oxygen breathing gas to the patient during said method.

21. The method of claim 14, wherein the amount of oxygen carrier administered is between about 0.5 and 10 ml/kg, based on the body weight of the patient.

22. The method of claim 14, wherein said monitoring step is performed by assessing $PvO_2$.

23. The method of claim 22, wherein said assessing of said patient's $PvO_2$ is performed using a pulmonary artery catheter.

24. The method of claim 22, wherein said desired value of $PvO_2$ is about 40 mmHg.

25. The method of claim 14, wherein said monitoring step is performed periodically.

26. The method of claim 14, wherein said monitoring step is performed continuously.

* * * * *